United States Patent
Mok et al.

(10) Patent No.: US 10,953,191 B2
(45) Date of Patent: Mar. 23, 2021

(54) DISPLAY APPARATUS, AND DISPLAY CONTROL METHOD AND APPARATUS OF THE DISPLAY APPARATUS

(71) Applicant: Samsung Display Co., Ltd., Yongin-si (KR)

(72) Inventors: Rangkyun Mok, Yongin-si (KR); Jongin Baek, Yongin-si (KR); Ilnam Kim, Yongin-si (KR); Wonsang Park, Yongin-si (KR)

(73) Assignee: Samsung Display Co., Ltd., Yongin-si (KR)

(*) Notice: Subject to any disclaimer, the term of this patent is extended or adjusted under 35 U.S.C. 154(b) by 82 days.

(21) Appl. No.: 14/863,227

(22) Filed: Sep. 23, 2015

(65) Prior Publication Data
US 2016/0121073 A1    May 5, 2016

(30) Foreign Application Priority Data

Nov. 3, 2014   (KR) .......................... 10-2014-0151589

(51) Int. Cl.
*A61M 21/02* (2006.01)
*G09G 3/20* (2006.01)
*A61N 5/06* (2006.01)
*A61M 21/00* (2006.01)

(52) U.S. Cl.
CPC ........... *A61M 21/02* (2013.01); *A61N 5/0618* (2013.01); *G09G 3/20* (2013.01); *G09G 3/2003* (2013.01); *A61M 2021/005* (2013.01); *A61M 2021/0083* (2013.01); *A61M 2205/3306* (2013.01); *A61N 2005/0626* (2013.01); *A61N 2005/0662* (2013.01); *A61N 2005/0663* (2013.01); *G09G 2300/0452* (2013.01); *G09G 2380/08* (2013.01)

(58) Field of Classification Search
CPC combination set(s) only.
See application file for complete search history.

(56) References Cited

U.S. PATENT DOCUMENTS

| | | | |
|---|---|---|---|
| 8,646,939 B2 | 2/2014 | Bues et al. | |
| 9,743,487 B2 | 8/2017 | Kato et al. | |
| 2009/0281604 A1* | 11/2009 | De Boer | A61M 21/00 607/88 |
| 2010/0033456 A1* | 2/2010 | Yoshida | G09G 3/3648 345/207 |
| 2010/0264850 A1* | 10/2010 | Yamamoto | G09G 3/3413 315/312 |
| 2011/0012820 A1* | 1/2011 | Kim | G09G 3/3208 345/82 |

(Continued)

FOREIGN PATENT DOCUMENTS

| CN | 101765878 A | 6/2010 |
|---|---|---|
| CN | 10-1984487 A | 3/2011 |

(Continued)

*Primary Examiner* — William Boddie
*Assistant Examiner* — Alecia D English
(74) *Attorney, Agent, or Firm* — Lewis Roca Rothgerber Christie LLP (57) ABSTRACT

A display panel including a plurality of pixels including a first pixel including a first blue sub-pixel, and a second pixel including a second blue sub-pixel, the second blue sub-pixel being configured to emit light having a wavelength different from that of the first blue sub-pixel and being adjacent to the first pixel.

10 Claims, 8 Drawing Sheets

(56) References Cited

U.S. PATENT DOCUMENTS

| | | | |
|---|---|---|---|
| 2011/0273494 A1 | 11/2011 | Jun | |
| 2012/0049726 A1* | 3/2012 | Yoo | H01L 27/3213 313/504 |
| 2012/0120043 A1 | 5/2012 | Cho et al. | |
| 2013/0100172 A1* | 4/2013 | Hou | G09G 3/3648 345/690 |
| 2013/0241946 A1* | 9/2013 | Jeong | G09G 3/2074 345/589 |
| 2014/0071030 A1 | 3/2014 | Lee | |
| 2014/0098143 A1* | 4/2014 | Lee | G09G 3/2003 345/690 |
| 2015/0015590 A1* | 1/2015 | Jeong | G09G 3/2003 345/502 |
| 2015/0091952 A1* | 4/2015 | Wu | G09G 3/20 345/690 |
| 2015/0130868 A1* | 5/2015 | Feng | G09G 3/2003 345/694 |
| 2016/0055781 A1* | 2/2016 | Phan | G09G 3/2003 345/690 |
| 2016/0180780 A1* | 6/2016 | Chen | G09G 3/3413 345/207 |
| 2016/0225300 A1* | 8/2016 | Jung | G09G 3/006 |

FOREIGN PATENT DOCUMENTS

| | | |
|---|---|---|
| CN | 102301410 A | 12/2011 |
| CN | 103745684 A | 4/2014 |
| JP | 2009-533127 A | 9/2009 |
| KR | 10-2012-0052739 A | 5/2012 |
| KR | 10-1146992 B1 | 5/2012 |
| KR | 10-2014-0035239 A | 3/2014 |
| KR | 10-2014-0044564 A | 4/2014 |
| KR | 10-2014-0044568 A | 4/2014 |

* cited by examiner

DISPLAY APPARATUS, AND DISPLAY CONTROL METHOD AND APPARATUS OF THE DISPLAY APPARATUS

CROSS-REFERENCE TO RELATED APPLICATION

This application claims priority to and the benefit of Korean Patent Application No. 10-2014-0151589, filed on Nov. 3, 2014, in the Korean Intellectual Property Office, the disclosure of which is incorporated herein in its entirety by reference.

BACKGROUND

1. Field

One or more exemplary embodiments relate to a display apparatus and a display control method and apparatus of the display apparatus.

2. Description of the Related Art

From among hormones produced in the body, Melatonin serves as an internal bio-clock: Melatonin is secreted to the entire body system at night and informs the body that it is nighttime. Melatonin helps one to fall asleep.

When morning comes, morning light inhibits the secretion of melatonin and then the low level of melatonin helps one to wake up. For example, it is known that when the body recognizes light having a wavelength of about 464 nm, the secretion of melatonin is inhibited, which means that the body may distinguish day and night depending on the recognition of the light having a wavelength of about 464 nm. Generally, people recognize light having a center wavelength of about 470 nm as blue light, and thus, the light having a wavelength of about 464 nm may be considered to be blue light.

SUMMARY

Aspects of embodiments of the present invention are directed to a display apparatus and a display control method and a device of the display apparatus having a waking effect or a sleep inducing effect.

Additional aspects will be set forth in part in the description that follows and, in part, will be apparent from the description, or may be learned by practice of the described exemplary embodiments.

According to one or more exemplary embodiments, there is provided a display panel including: a plurality of pixels including: a first pixel including a first blue sub-pixel, and a second pixel including a second blue sub-pixel, the second blue sub-pixel being configured to emit light having a wavelength different from that of the first blue sub-pixel and being adjacent to the first pixel.

In an embodiment, the first pixel further includes a sub-pixel configured to emit a light having a color different from blue, and the second pixel includes another sub-pixel configured to emit a same color light as emitted from the sub-pixel of the first pixel.

In an embodiment, a center wavelength of light emitted from the first blue sub-pixel is lower than a center wavelength of light emitted from the second blue sub-pixel.

In an embodiment, the center wavelength of the light emitted from the first blue sub-pixel is about 450 nm, and the center wavelength of the light emitted from the second blue sub-pixel is about 464 nm.

In an embodiment, the first pixel includes a first sub-pixel group including a red pixel and a green pixel, and a second sub-pixel group including a first blue pixel and a green pixel, the second pixel includes a third sub-pixel group including a red pixel and a green pixel, and a fourth sub-pixel group including a second blue pixel and a green pixel, wherein one selected from the first blue pixel and the second blue pixel and a red pixel of the third or fourth sub-pixel group are alternately arranged in a first direction in a first sub-pixel column, and at least two of the green pixels of the first, second, third, and fourth sub-pixel group is arranged in the first direction in a second sub-pixel column.

In an embodiment, the first sub-pixel column has the red pixel, the first blue pixel, the red pixel, and the second blue pixel in an order as stated.

In an embodiment, the first sub-pixel column includes a 1-1 sub-pixel column in which the red pixel and the first blue pixel are alternately arranged, and a 1-2 sub-pixel column in which the red pixel and the second blue pixel are alternately arranged.

In an embodiment, the red pixel in the 1-1 sub-pixel column and the second blue pixel in the 1-2 sub-pixel column are arranged horizontally, and the first blue pixel in the 1-1 sub-pixel column and the red pixel in the 1-2 sub-pixel column are arranged horizontally.

According to one or more exemplary embodiments, there is provided a display control method of a display panel, the display control method including: setting a display mode of the display panel to one selected from a first mode using a first blue sub-pixel, a second mode using a second blue sub-pixel, and a third mode using the first blue sub-pixel and the second blue sub-pixel to emit blue light; and generating an output signal to use the first blue sub-pixel when the display mode is the first mode, to use the second blue sub-pixel for the second mode, and to use both the first blue sub-pixel and the second blue sub-pixel for the third mode, wherein the display panel is configured to emit light corresponding to the output signal, wherein the display panel includes a first pixel including the first blue sub-pixel and a second pixel including the second blue sub-pixel, the second blue sub-pixel being configured to emit light having a wavelength different from that of the first blue sub-pixel, and wherein the second pixel is adjacent to the first pixel.

In an embodiment, a center wavelength of light emitted from the first blue sub-pixel is lower than a center wavelength of light emitted from the second blue sub-pixel.

In an embodiment, in the setting the display mode of the display panel, a current state is determined as day or night, wherein when the current state is day, the display mode is set to the second mode or the third mode and when the current state is night, the display mode is set to the first mode.

In an embodiment, in the setting the display mode of the display panel, a current state is determined as day or night based on at least one selected from a current time, a pre-set display mode change cycle, or external illumination, and the display mode is set based on the current state.

According to one or more exemplary embodiments, there is provided a display control apparatus of a display panel, the apparatus including: a display mode controller configured to set a display mode of the display panel to one selected from a first mode using a first blue sub-pixel, a second mode using a second blue sub-pixel, and a third mode using both the first blue sub-pixel and the second blue sub-pixel to emit blue light; and an output signal generator configured to generate an output signal to use the first blue sub-pixel when the display mode is the first mode, to use the second blue sub-pixel for the second mode, and to use the first blue sub-pixel and the second blue sub-pixel for the third mode, wherein the display panel is configured to emit light corresponding to the output signal, wherein the display panel includes a first pixel including the first blue sub-pixel and a second pixel including the second blue sub-pixel, the second blue sub-pixel being configured to emit light having a wavelength different from that of the first blue sub-pixel, and wherein the second pixel is adjacent to a first pixel.

In an embodiment, a center wavelength of light emitted from the first blue sub-pixel is lower than a center wavelength of light emitted from the second blue sub-pixel.

In an embodiment, the display mode controller is further configured to determine a current state as day or night, and when the current state is day, to set the display mode to the second mode or the third mode, and when the current state is night, to set the display mode to the first mode.

In an embodiment, the display mode controller is further configured to determine a current state as day or night based on at least one selected from a current time, a pre-set display mode change cycle, or external illumination, and to set the display mode based on the current state.

In an embodiment, the display mode controller is further configured to determine a current state as day or night based on at least one selected from a current time, a pre-set display mode change cycle, or external illumination, and to set the display mode based on the current state.

In an embodiment, the display mode controller is further configured to determine a current state as, day or night based on at least one selected from a current time, a pre-set display mode change cycle, or external illumination, and to set the display mode based on the current state.

These general and specific embodiments may be implemented by using a system, a method, a computer program, or a combination of the system, the method, and the computer program.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

The present invention will be described more fully with reference to the accompanying drawings, in which exemplary embodiments of the invention are shown. The present invention may, however, be embodied in many different forms and should not be construed as being limited to the exemplary embodiments set forth herein; rather these exemplary embodiments are provided so that this disclosure will be thorough and complete, and will fully convey the concept of the present invention to one of ordinary skill in the art.

In the drawings, like reference numerals denote like elements and the detailed descriptions thereof may not be repeated.

It will be understood that, although the terms "first", "second", "third", etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section discussed below could be termed a second element, component, region, layer or section, without departing from the spirit and scope of the present invention.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "include," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the present invention refers to "one or more embodiments of the present invention." Also, the term "exemplary" is intended to refer to an example or illustration.

As used herein, the term "substantially," "about," and similar terms are used as terms of approximation and not as terms of degree, and are intended to account for the inherent variations in measured or calculated values that would be recognized by those of ordinary skill in the art.

As used herein, the terms "use," "using," and "used" may be considered synonymous with the terms "utilize," "utilizing," and "utilized," respectively.

The display apparatus and/or any other relevant devices or components according to embodiments of the present invention described herein may be implemented utilizing any suitable hardware, firmware (e.g. an application-specific integrated circuit), software, or a suitable combination of software, firmware, and hardware. For example, the various components of the display apparatus may be formed on one integrated circuit (IC) chip or on separate IC chips. Further, the various components of the display apparatus may be implemented on a flexible printed circuit film, a tape carrier package (TCP), a printed circuit board (PCB), or formed on a same substrate as the display apparatus. Further, the various components of the display apparatus may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

In the following description of the present invention, the sizes of constituent elements shown in the drawings may be exaggerated, or sometimes the elements may be omitted to aid in the better understanding of the present invention. However, such ways of description do not limit the scope of the technical concept of the present invention.

Figure 1:
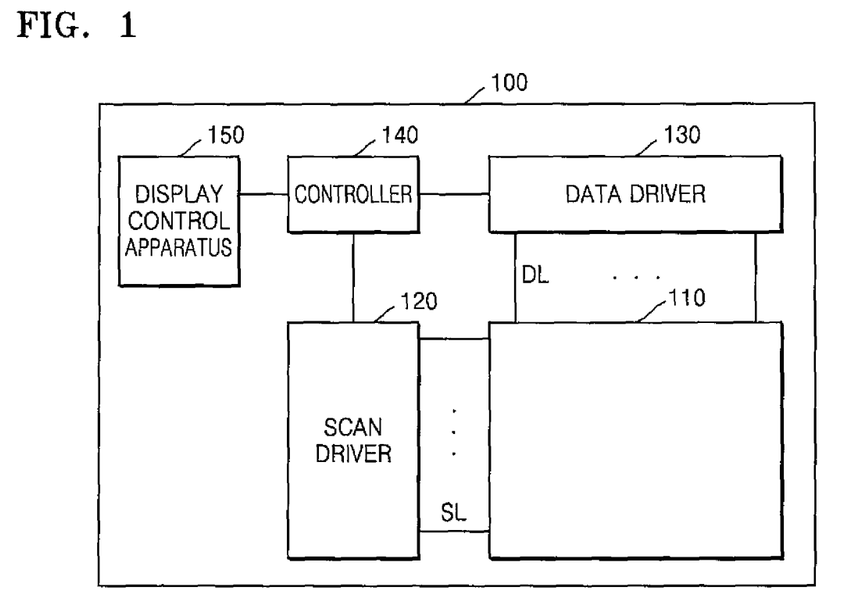
FIG. 1 is a block diagram showing a display apparatus according to an exemplary embodiment of the inventive concept.

FIG. 1 is a block diagram showing a display apparatus 100 according to an exemplary embodiment of the inventive concept.

Referring to FIG. 1, the display apparatus 100 includes a display panel 110, a scan driver 120, a data driver 130, a controller 140, and a display control apparatus 150.

The display panel 110 includes a plurality of pixels and displays an image by emitting light according to a signal transmitted from the scan driver 120 and the data driver 130.

The data driver 130 converts an image signal into an analog or digital data signal according to a control of the controller 140 (e.g. according to a control signal from the controller 140) and then transmits the analog or digital data signal to data lines DL.

The scan driver 120 generates a scan pulse according to a control of the controller 140 and then sequentially transmits the scan pulse to scan lines SL in order to select a horizontal line to which a data voltage is to be applied.

The controller 140 controls the data driver 130 and the scan driver 120.

The display control apparatus 150 generally controls a display on the display apparatus 100. According to an exemplary embodiment of the inventive concept, the display control apparatus 150 sets a display mode of the display apparatus 100, generates an output signal according to the display mode, and supplies the controller 140 with the output signal.

The display apparatus 100 according to an exemplary embodiment of the inventive concept may have a waking effect or sleep inducing effect. It is known that when the body recognizes light having a wavelength of about 464 nm, the secretion of melatonin is inhibited. Melatonin is hormone that helps one to fall asleep.

A display apparatus displays an image by using a plurality of sub-pixels that emit different lights. For example, a display apparatus includes sub-pixels in which each of the sub-pixels emits red, green, or blue light. Here, the blue light mainly includes light having a wavelength of about 464 nm, and thus, hinders the ability of a user who is viewing the display apparatus to fall asleep.

The display apparatus 100 according to an exemplary embodiment of the inventive concept includes two kinds of blue sub-pixels having different center wavelengths. For example, the display apparatus 100 according to an exemplary embodiment may include a first blue sub-pixel for emitting a first blue light having a center wavelength that is far from 464 nm and a second blue sub-pixel for emitting a second blue light having a center wavelength that is close to 464 nm. For example, the first blue sub-pixel may emit dark blue light, whereas the second blue sub-pixel may emit cyan blue light. The center wavelength of the first blue light may be shorter than the center wavelength of the second blue light. The center wavelength of the first blue light may be in a range of about 440 nm and about 450 nm, and the center wavelength of the second blue light may in a range of about 460 nm and about 470 nm. As an example, a first and second blue sub-pixel may be formed such that the center wavelength of the first blue light emitted from the first blue sub-pixel may be 450 nm and the center wavelength of the second blue light emitted from the second blue sub-pixel may be 464 nm.

The center wavelength of light emitted from the first blue sub-pixel is far from 464 nm, and thus, has a little melatonin inhibition effect. However, the center wavelength of light emitted from the second blue sub-pixel is close to 464 nm and thus inhibits melatonin secretion. In this regard, the light emitted from the first blue sub-pixel does not hinder the ability of a viewer to fall asleep, and may help the viewer to fall asleep, whereas the light emitted from the second blue sub-pixel awakens the viewer. The display apparatus 100 according to an exemplary embodiment appropriately drives the two blue sub-pixels according to the display mode, and thus, wakes the viewer up or helps the viewer to fall asleep.

Hereinafter a structure of pixels and a driving method of the pixel according to one or more exemplary embodiments of the inventive concept will be explained with reference to the accompanying drawings.

Figure 2A:
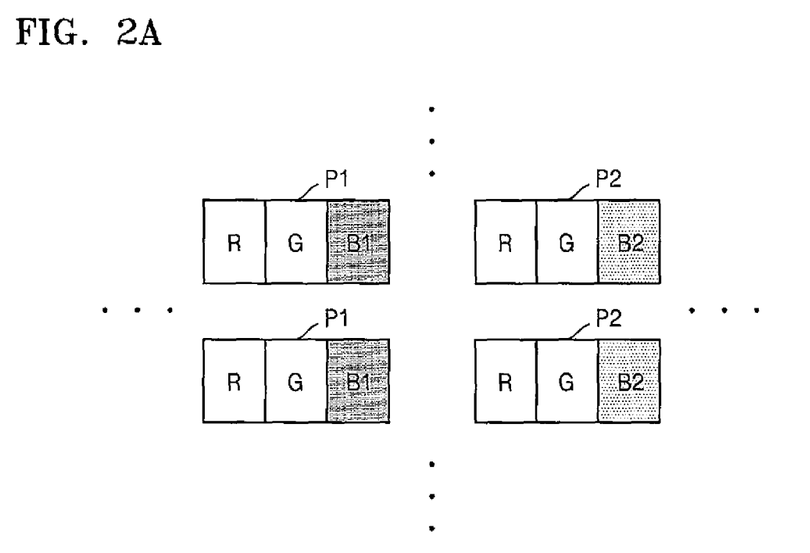
FIG. 2A is a schematic view showing a structure of pixels according to an exemplary embodiment of the inventive concept.

FIG. 2A is a schematic view showing a structure of pixels according to an exemplary embodiment of the inventive concept.

Referring to FIG. 2A, the display panel 110 of FIG. 1 may include different kinds of pixels, for example, a first pixel P1 and a second pixel P2. Each of the first pixel P1 and the second pixel P2 may include a plurality of sub-pixels. Referring to FIG. 2A, each of the first pixel P1 and the second pixel P2 may include different color sub-pixels or identical color sub-pixels. In FIG. 2A, the first pixel P1 and the second pixel P2 commonly include a red sub-pixel R and a green sub-pixel G. The first pixel P1 further includes a first blue sub-pixel B1. The second pixel P2 further includes a second blue sub-pixel B2.

The first blue sub-pixel B1 and the second blue sub-pixel B2 emit blue light having different center wavelengths from each other. For example, the first blue sub-pixel B1 may emit dark blue light, while the second blue sub-pixel B2 may emit cyan blue light. The center wavelength of the dark blue light emitted from the first blue sub-pixel B1 may be shorter than the center wavelength of the cyan blue light emitted from the second blue sub-pixel B2. The center wavelength of the light emitted from the first blue sub-pixel B1 may be in a range of about 440 nm to about 450 nm, and the center wavelength of the light emitted from the second blue sub-pixel B2 may be in a range of about 460 nm to about 470 nm. As an example, the center wavelength of the light emitted from the first blue sub-pixel B1 is 450 nm, and the center wavelength of the light emitted from the second blue sub-pixel B2 is 464 nm.

As illustrated in FIG. 2A, the first pixel P1 and the second pixel P2 may be located adjacent to each other. Although 4 pixels are illustrated in FIG. 2A as a part of pixels located in the display panel 110, the display panel 110 may include more pixels than illustrated in FIG. 2A. For example, a pixel row exclusively consisting of the first pixels P1 and another pixel row exclusively consisting of the second pixels P2 may be alternately located in the display panel 110.

Figure 2B:
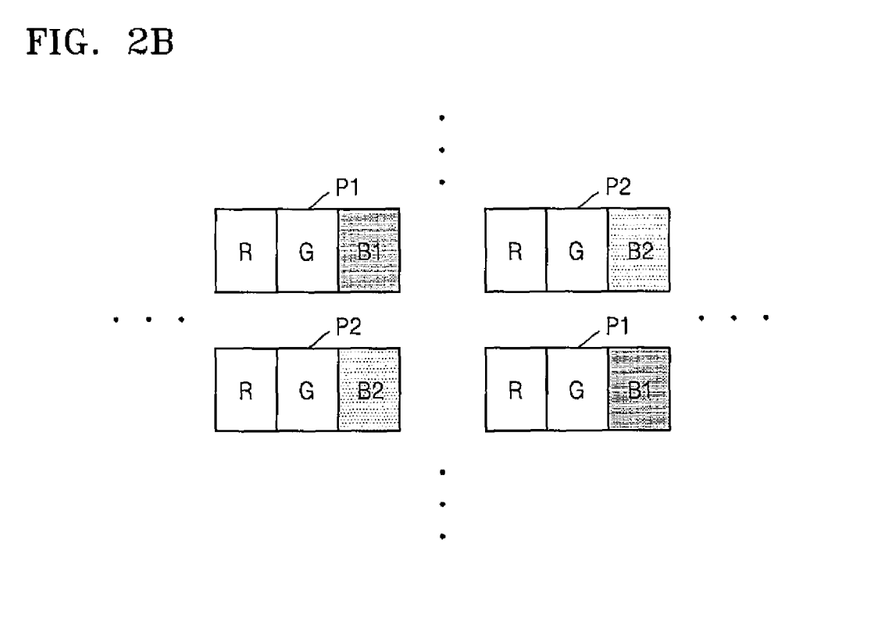
FIG. 2B is a view showing another example of a structure of pixels of FIG. 2A.

FIG. 2B is a view showing another example of a structure of pixels of FIG. 2A.

Referring to a structure of pixels illustrated in FIG. 2B, the first pixels P1 and the second pixels P2 may be located adjacent vertically and horizontally. For example, in the structure of pixels illustrated in FIG. 2B, the first pixels P1 are located to surround the second pixel P2, and the second pixels P2 are located to surround the first pixel P1. In a pixel row, the first pixel P1 and the second pixel P2 are alternately located. Also, in a pixel column, the first pixel. P1 and the second pixel P2 are alternately located.

The sub-pixels included in the first pixel P1 and the second pixel P2 in FIG. 2B are the same or substantially the same as in FIG. 2A, and thus detailed descriptions thereof will not be repeated herein.

Figure 3:
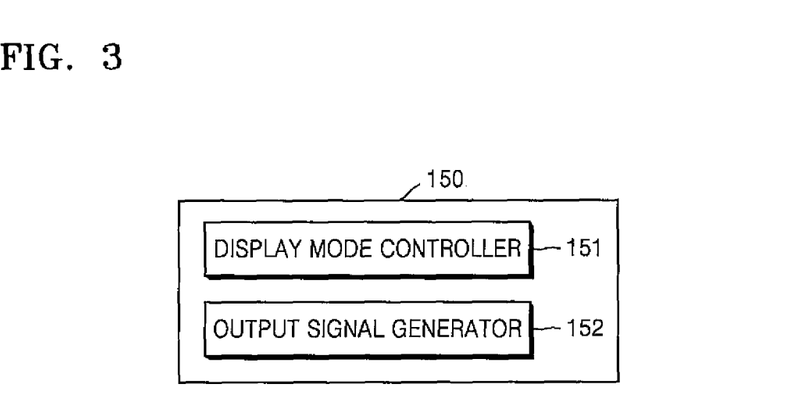
FIG. 3 is a block diagram showing a structure of the display control apparatus 150 in FIG. 1.

FIG. 3 is a block diagram showing a structure of the display control apparatus 150 in FIG. 1.

Only essential elements for understanding operation of the display control apparatus 150 are illustrated in FIG. 3 for convenience of description. Therefore, any one of ordinary skill in the art may understand that besides the elements illustrated in FIG. 3 other elements commonly used may be further included.

The display control apparatus 150 according to an exemplary embodiment may correspond to at least one processor. In this regard, the display control apparatus 150 may be driven while being included in another hardware apparatus such as a microprocessor or a commonly-used computer system.

Referring to FIG. 3, the display control apparatus 150 according to exemplary embodiment of the inventive concept includes a display mode controller 151 and an output signal generator 152. The display mode controller 151 and the output signal generator 152 may be included in two respective semiconductor chips or may be included in one semiconductor chip.

The display mode controller 151 according to an exemplary embodiment sets a display mode of the display panel 110. The display mode may vary depending on which blue sub-pixel is used. For example, the display mode may include a first mode using the first blue sub-pixel, a second mode using the second blue sub-pixel, and a third mode using both the first and second blue sub-pixels, in order to display blue light.

The display mode controller 151 may select, for example, the first mode for helping a viewer to fall asleep, or the second mode for waking the viewer up, or the third mode as a general display mode. The display mode may be selected based on a current time, external illumination sensed by an illumination sensor, or a mode change cycle set by the user.

For example, the display mode controller 151 may select the second mode for day and the first mode for night based on the current time. Alternatively, the display mode controller 151 may select the third mode regardless of time. The display mode controller 151 may select the first mode when the external illumination is high or the second mode when the external illumination is low. The display mode controller 151 may select the display mode according to the mode change cycle that is pre-set by the user.

The output signal generator 152 according to an exemplary embodiment generates an output signal that is to be applied to the display panel 110. The output signal generator 152 outputs the generated output signal to the controller 140, and the controller 140 applies the output signal to the display panel 110 through the scan driver 120 and the data driver 130.

Regarding the display mode of the display panel 110 described above, a driving method of the pixel varies depending on the display mode. For example, pixels emitting blue light from among pixels displaying an image may vary depending on the display mode. The output signal generator 152 generates the output signal corresponding to the display mode of the display panel 110. For example, when the display mode of the display panel 110 is the first mode, the output signal generator 152 generates an output signal in order for the first blue sub-pixel to be used. In this case, a pixel value of the second blue sub-pixel may be output as 0. When the display mode of the display panel 110 is the second mode, the output signal generator 152 generates the output signal in order for the second blue sub-pixel to be used. In this case, a pixel value of the first blue sub-pixel may be output as 0. When the display mode of the display panel 110 is the third mode, the output signal generator 152 generates the output signal in order for both the first blue sub-pixel and the second blue sub-pixel to be used.

For example, when the output signal is generated by using an image signal including color data of red, green, and blue, the output signal generator 152 may use the image signal, as is (e.g., without alteration) to generate the output signal under the third mode. However, when the display mode of the display panel 110 is the first mode or the second mode, the output signal generator 152 alters the image signal to generate the output signal in which blue pixel values of some pixels are 0.

The output signal generator 152 may distribute to adjacent pixels a pixel value that was originally assigned to a pixel now having the pixel value of 0. For example, when a blue pixel value of a certain pixel including the first blue sub-pixel is changed to 0, the blue pixel value that was assigned to the certain pixel in an original image may be distributed and added to a blue pixel value of pixels including the second blue sub-pixel from among adjacent pixels around the certain pixel. Therefore, the blue pixel value of the adjacent pixels may be increased.

Figure 4:
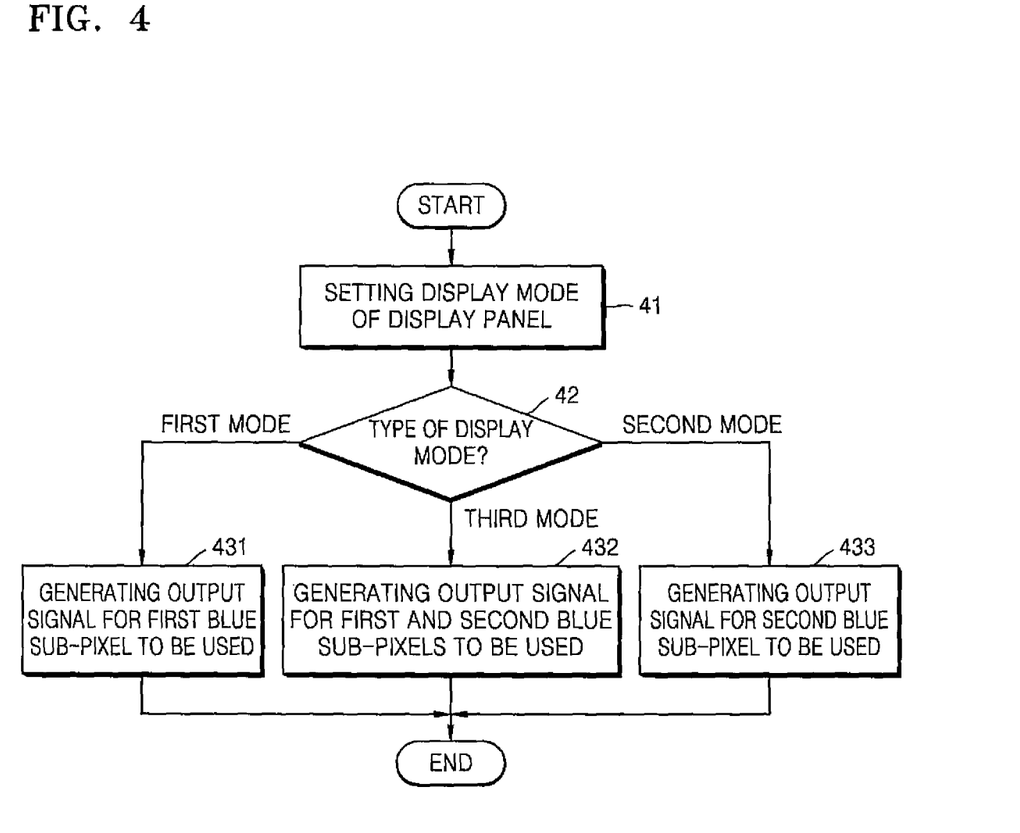
FIG. 4 is a flow diagram of a display control method according to an exemplary embodiment of the inventive concept.

FIG. 4 is a flow diagram of a display control method according to an exemplary embodiment of the inventive concept.

The flow diagram illustrated in FIG. 4 shows operations performed by the display control apparatus 150 illustrated in FIG. 3. The foregoing descriptions of the structure illustrated in FIG. 3 also apply to the display control method of FIG. 4.

Referring to FIG. 4, in operation 41, the display mode controller 151 in FIG. 3 sets a display mode of a display panel. The display mode controller 151 may set the display mode depending on a current status. For example, the current status may be set to day or night. When the current status is day, the display mode may be set to the second mode or the third mode, and when the current status is night, the display mode may be set to the first mode. The display mode controller 151 may recognize the current status as day or night based on at least one selected from current time, a pre-set display mode change cycle, and external illumination.

In operation 42, the display control method performed by the output signal generator 152 in FIG. 3 proceeds to any one of operations 431 to 433 according to the display mode of the display panel set in operation 41. When the display mode is the first mode, operation 431 is performed, when the display mode is the third mode, operation 432 is performed, and when the display mode is the second mode, operation 433 is performed.

In operation 431, the output signal generator 152 generates an output signal to display an image by using the first blue sub-pixel according to the display mode of the first mode.

In operation 432, the output signal generator 152 generates an output signal to display an image by using the first blue sub-pixel and the second blue sub-pixel according to the display mode of the third mode.

In operation 433, the output signal generator 152 generates an output signal to display an image by using the second blue sub-pixel according to the display mode of the second mode.

Figure 5A:
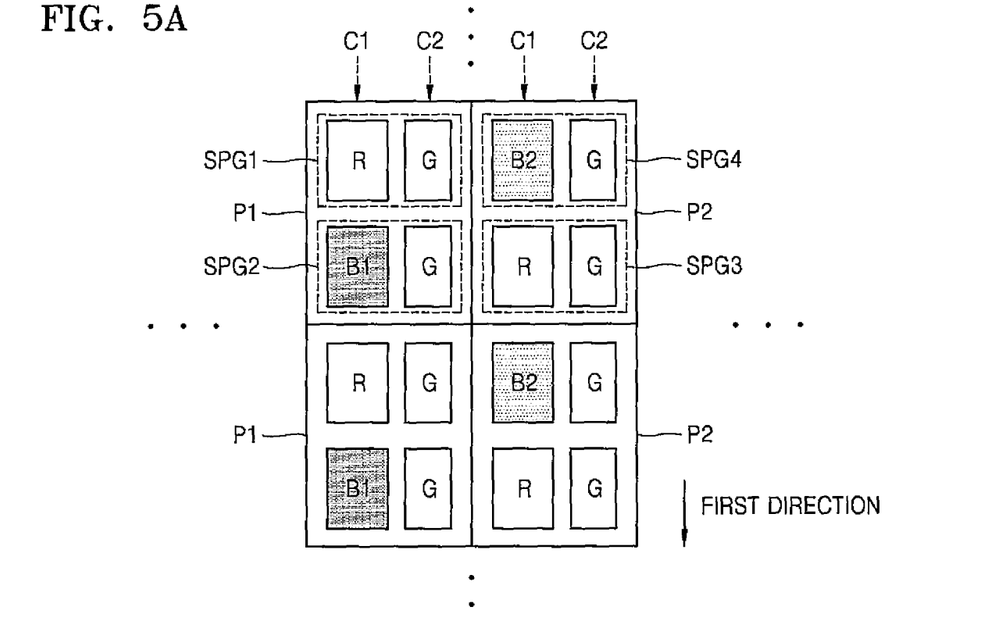
FIG. 5A is a schematic view showing another example of a pixel structure according to an exemplary embodiment of the inventive concept.

FIG. 5A is a schematic view showing another example of a pixel structure according to an exemplary embodiment of the inventive concept.

The pixel structure illustrated in FIG. 5A shows a pixel structure arranged in the display panel 110 according to an exemplary embodiment of the inventive concept. When a panel of the display apparatus displays an image by using red, green, and blue sub-pixels, the sub-pixels may be arranged in various suitable ways. For example, the sub-pixels may be arranged in a stripe structure in which a unit pixel includes one sub-pixel of respective red, green, and blue and each sub-pixel is arranged in a row; or a structure in which a unit pixel includes only some of the sub-pixels, or two or more of some of the sub-pixels, such as a pentile structure in which the unit pixel includes each one of the red and the blue sub-pixels, and two green sub-pixels.

The pixel structure in FIG. 5A shows an example of the pentile structure according to an exemplary embodiment of the inventive concept. An outer line of a rectangle (e.g., a square) denotes a pixel. Referring to FIG. 5A, the display panel 110 includes a first pixel P1 and a second pixel P2. The first pixel P1 includes a red sub-pixel (hereinafter, sub-pixel R), a first blue sub-pixel (hereinafter, sub-pixel B1), and two green sub-pixels (hereinafter, sub-pixels G). The second pixel P2 includes the sub-pixel R, a second blue sub-pixel (hereinafter, sub-pixel B2), and two sub-pixels G. A unit pixel may have two sub-pixels therein. The first pixel P1 includes a first sub-pixel group SPG1 including the sub-pixels R and G and a second sub-pixel group SPG2 including the sub-pixels B1 and G. The second pixel P2 includes a third sub-pixel group SPG3 including the sub-pixels R and G, and a fourth sub-pixel group SPG4 including the sub-pixels B2 and G.

According to an exemplary embodiment, the first pixel P1 and the second pixel P2 are located adjacent to each other. Referring to FIG. 5A, columns of the first pixel P1 and the second pixel P2 are alternately arranged in the display panel 110 according to an exemplary embodiment.

Referring to FIG. 5A, the pixel structure of the display panel 110 according to an exemplary embodiment has a first sub-pixel column C1 and a second sub-pixel column C2 that are alternately arranged. The sub-pixels B1 and B2 and sub-pixel R may be alternately arranged in a first direction in the first sub-pixel column C1, and the sub-pixel G may be arranged in the first direction in the second sub-pixel column C2. For example, in FIG. 5A, the sub-pixels R and B1 are alternately arranged or the sub-pixels R and B2 are alternately arranged in the first sub-pixel column C1.

Figure 5B:
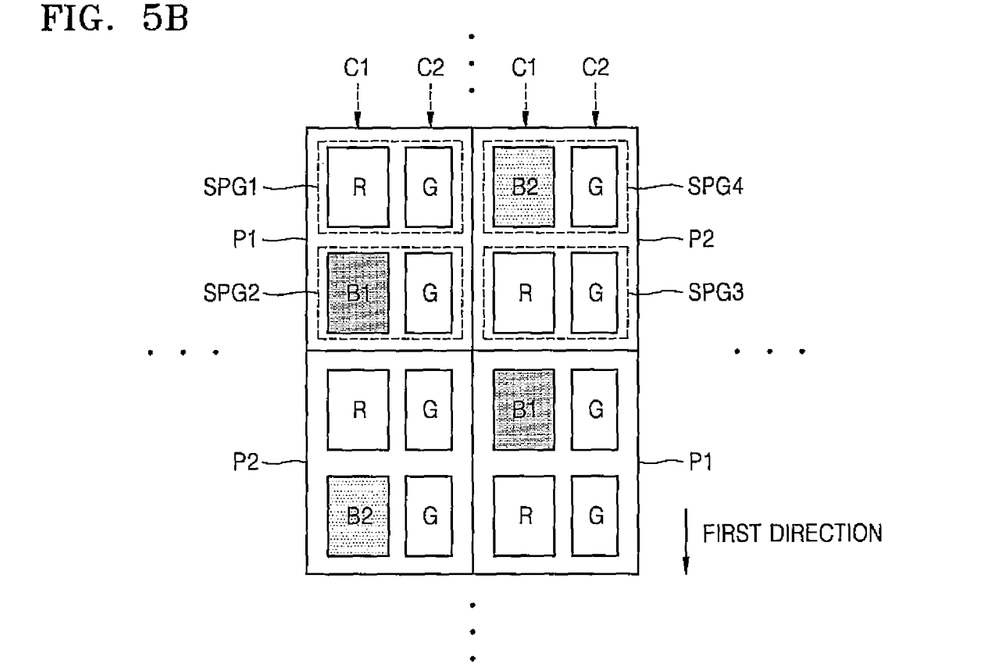
FIG. 5B is a view showing another example of FIG. 5A.

FIG. 5B is a view showing another example of FIG. 5A.

Referring to FIG. 5B, the first pixel P1 and the second pixel P2 are alternately arranged so that identical pixels are not located adjacent to each other vertically or horizontally. The display panel 110 according to an exemplary embodiment has a pixel column in which the first pixel P1 and the second pixel P2 are alternately arranged.

A pixel structure of the display panel 110 according to an exemplary embodiment has a first sub-pixel column C1 and a second sub-pixel column C2 that are alternately arranged. The sub-pixels B1 and B2 and the sub-pixel R are alternately arranged in the first sub-pixel column C1. For example, sub-pixels are arranged in an order of the sub-pixel R, the sub-pixel B1, the sub-pixel R, and the sub-pixel B2. The sub-pixel G may be arranged in the first direction in the second sub-pixel column C2 in the same manner as in FIG. 5A.

Figure 6A:
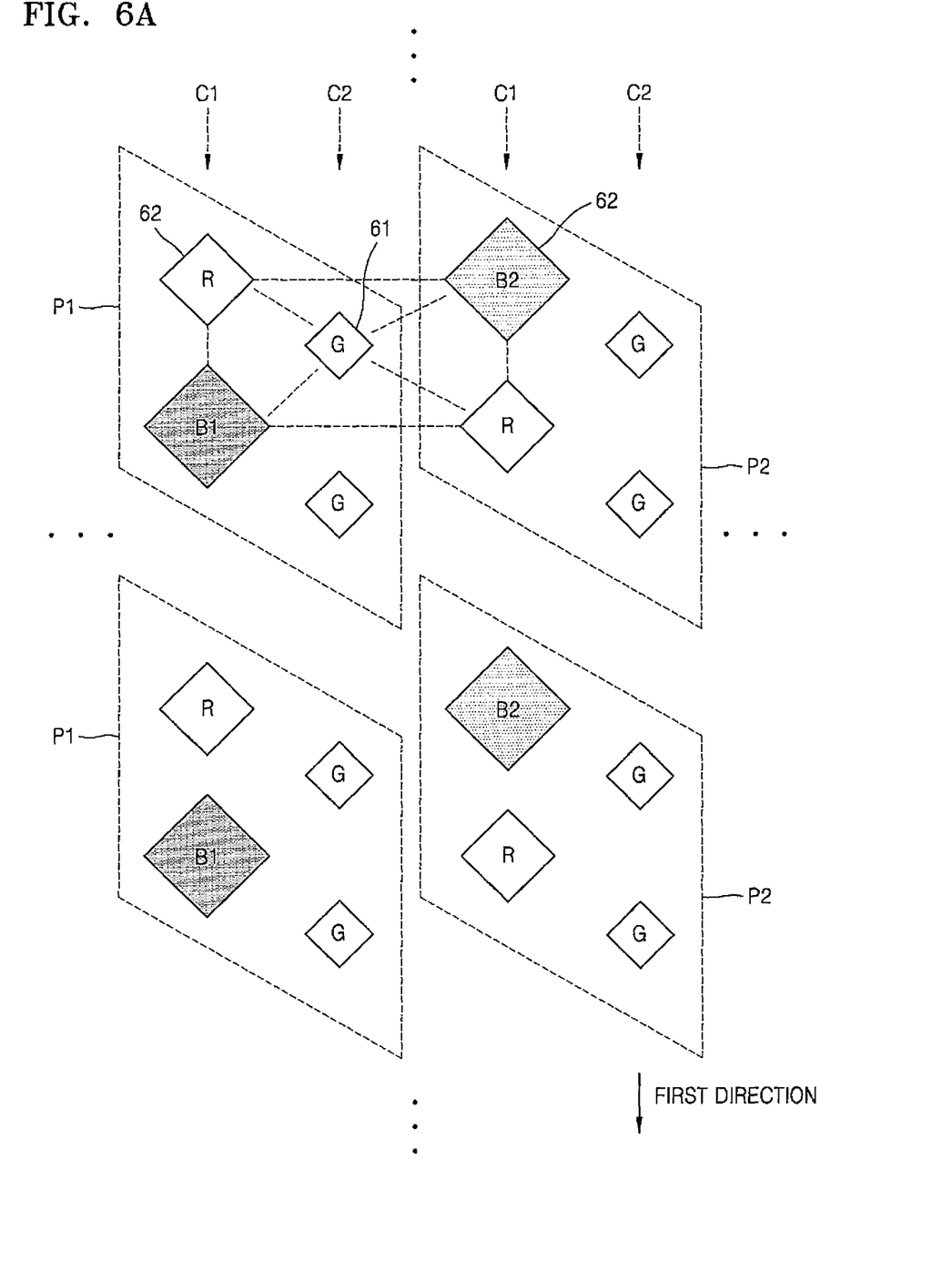
FIG. 6A is a schematic view showing a pixel structure according to another exemplary embodiment of the inventive concept.

FIG. 6A is a schematic view showing a pixel structure according to another exemplary embodiment of the inventive concept.

FIG. 6A shows the pixel structure according to another exemplary embodiment that is arranged in a pentile structure. A dashed line of a square denotes a pixel. Referring to FIG. 6A, the display panel 110 includes a first pixel P1 and a second pixel P2. The first pixel P1 includes a sub-pixel R, a sub-pixel B1, and two sub-pixels G. The second pixel P2 includes a sub-pixel R, a sub-pixel B2, and two sub-pixels G. According to an exemplary embodiment, the first pixel P1 and the second pixel P2 are located adjacent to each other. The display panel 110 according to an exemplary embodiment has a column of the first pixel P1 and a column of the second pixel P2 that are alternately arranged.

Referring to FIG. 6A, the display panel 110 according to an exemplary embodiment has a pixel structure in which a first sub-pixel column C1 and a second sub-pixel column C2 are alternately located. The sub-pixels B1 and B2 and the sub-pixel R may be alternately arranged in the first direction in the first sub-pixel column C1, and the sub-pixel G may be arranged in the first direction in the second sub-pixel column C2. For example, in FIG. 6A, the sub-pixels R and B1 or the sub-pixels R and B2 are alternately arranged in the first sub-pixel column C1.

In FIG. 6A, the sub-pixels included in the first sub-pixel column C1 and the second sub-pixel column C2 may be located in a zigzag manner in comparison to FIG. 5A. For example, each of pixels (62) included in the two first sub-pixel columns C1 adjacent to the second sub-pixel column C2 may be located at any corner of a square that is formed with a sub-pixel G (61) included in the second sub-pixel column C2 as a center thereof.

Figure 6B:
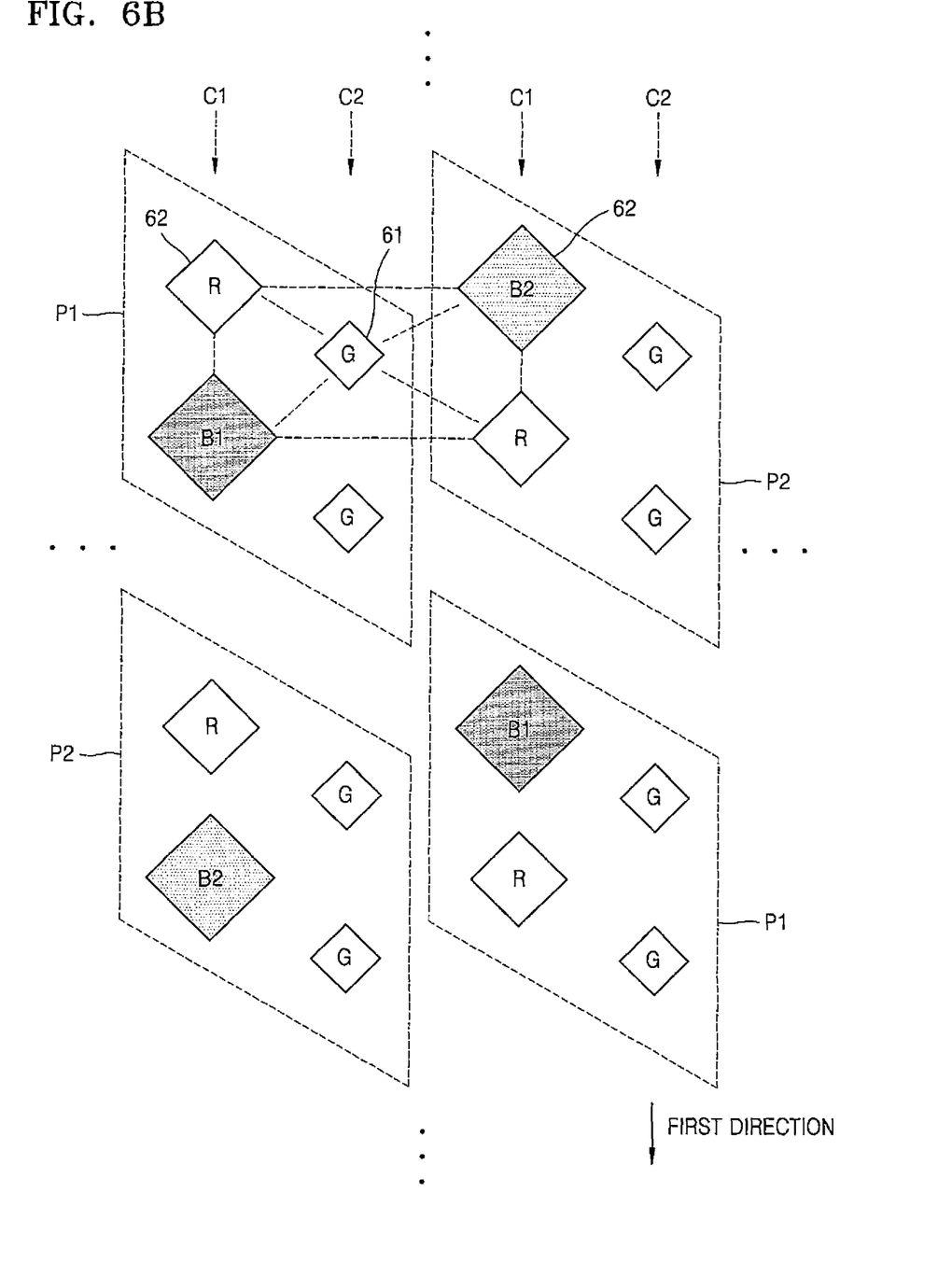
FIG. 6B is a view showing another example of FIG. 6A.

FIG. 6B is a view showing another example of FIG. 6A.

Referring to FIG. 6B, a first pixel P1 and a second pixel P2 are alternately located so that the identical pixels are not located adjacent to each other vertically and horizontally. The display panel 110 according to an exemplary embodiment has a pixel column in which the first pixel P1 and the second pixel P2 are alternately arranged.

Referring to FIG. 6B, the display panel 110 according to an exemplary embodiment has a pixel structure in which a first sub-pixel column C1 and a second sub-pixel column C2 are alternately located. The sub-pixels B1 and B2 and the sub-pixel R are alternately arranged in the first sub-pixel column C1, for example, a sub-pixel R, a sub-pixel B1, a sub-pixel R, and a sub-pixel B2 may be arranged in this stated order. The sub-pixel G may be arranged in the first direction in the second sub-pixel column C2 in the same manner as in FIG. 6A.

The pixel structures formed by using the pentile structure according to an exemplary embodiment of the inventive concept are described with reference to FIGS. 5A to 6B. When the pixel structure is formed in the pentile structure, the controller 140 includes an additional output signal conversion unit (converter), and thus, an output signal generated to correspond to a pixel in a general structure may be converted to an output signal corresponding to a pixel in a pentile structure. A basic principle that applies to a case in which the output signal generated to correspond to the pixel in the general structure (sub-pixels included in each pixel are the same or correspond to each other) is converted to the output signal corresponding to the pixel in the pentile structure (sub-pixels included in each pixel are different from each other) will be explained with reference to FIG. 7.

Figure 7:
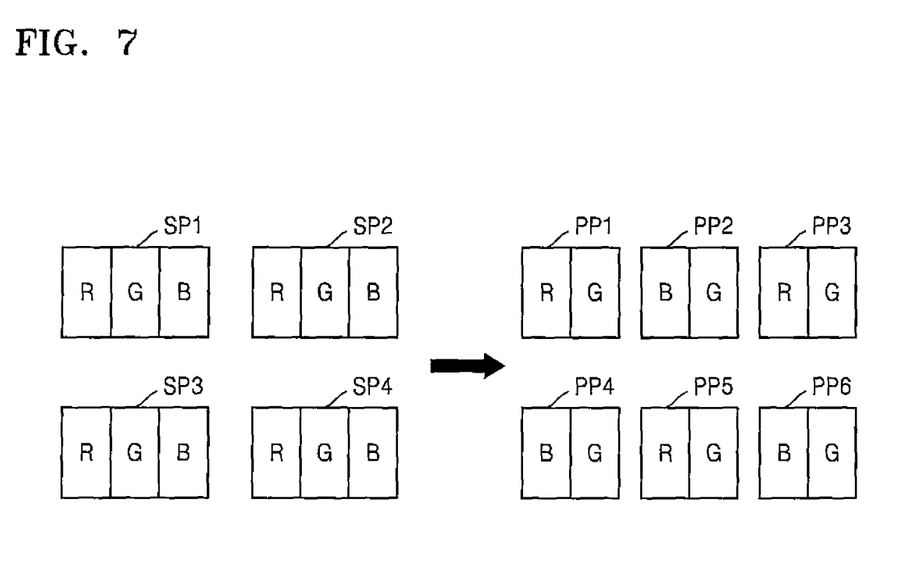
FIG. 7 is a view illustrating the conversion of an output signal corresponding to a pixel in a general structure to the output signal corresponding to a pixel in a pentile structure.

Referring to FIG. 7, an output signal conversion unit included in the controller 140 may receive input color data corresponding to a pixel structure formed in a stripe structure, and then convert the input color data to output color data corresponding to the pentile structure. For convenience, it is assumed that the input color data includes color data of red, green, and blue. Also, it is assumed that an image formed from input color data by pixels SP1, SP2, SP3, and SP4 that are arranged in the stripe structure and an image formed from output color data by pixels PP1, PP2, PP3, PP4, PP5, and PP6 that are arranged in the pentile structure are identical or substantially identical.

Input color data for a pixel SP1 may include blue color data. However, a pixel PP1 does not include a blue sub-pixel, and thus, output color data for the pixel PP1 may not include blue color data. In this regard, a color data conversion unit changes a color coordinate so that blue color data for the pixel SP1 is embodied by (e.g., displayed by) a pixel PP2 adjacent to the pixel PP1, and then output color data is generated from the pixel PP2. The color data conversion unit may be included in the display control apparatus 150.

Similarly, input color data for the pixel SP2 may include red color data. However, the pixel PP2 does not include a red sub-pixel, and thus, output color data for the pixel PP2 may not include red color data. In this regard, the color data conversion unit changes a color coordinate so that red color data for the pixel SP2 is embodied by (e.g., displayed by) a pixel PP3 adjacent to the pixel PP2, and then output color data is generated from the pixel PP3.

In short, the pixel PP2 may embody (e.g., display) the blue color data corresponding to the pixel PP1, and the pixel PP3 may embody the red color data corresponding to the pixel PP2.

The descriptions with reference to FIG. 7 are about the basic principle of converting the output signal to correspond to the pixel in the pentile structure; however, the inventive concept is not limited thereto.

The controller 140 or the display control apparatus 150 may include the output signal conversion unit. The display control apparatus 150 generates the output color data corresponding to the pentile structure based on the input color data including red, green, and blue color data by taking into account the display mode of the display panel 110.

Figure 8A:
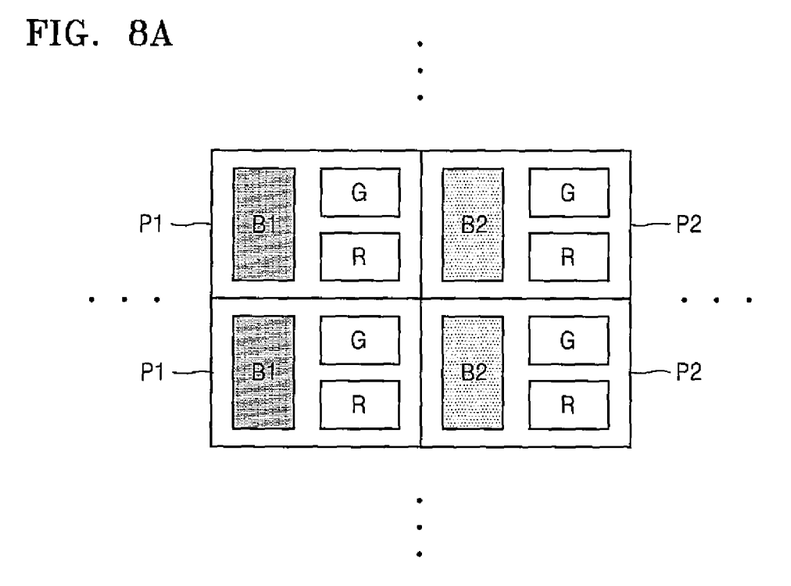
FIGS. 8A and 8B are schematic views showing pixel structures according to another exemplary embodiment of the inventive concept.
Figure 8B:
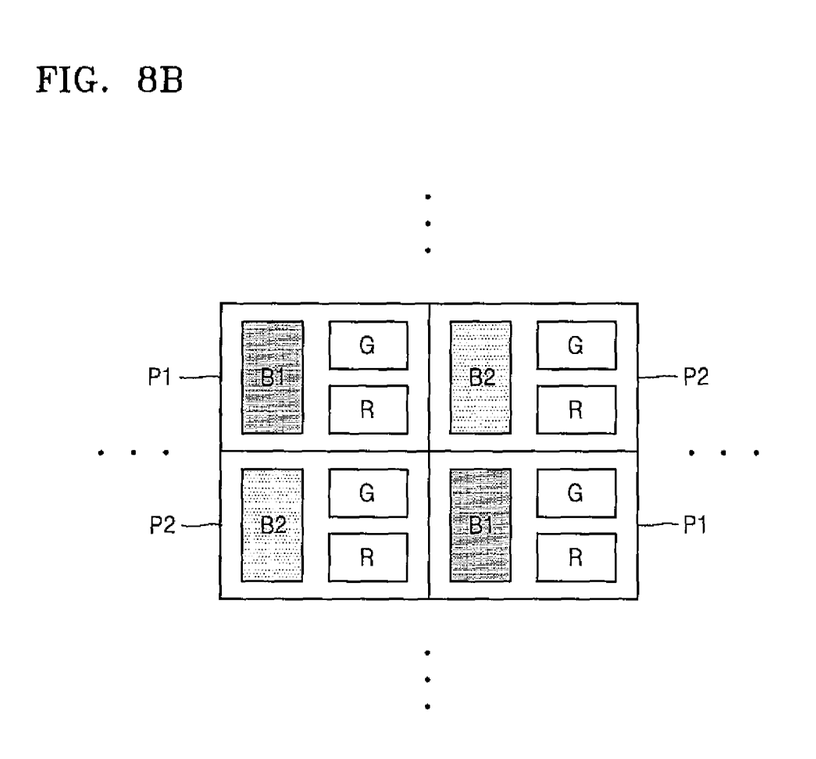

FIGS. 8A and 8B are schematic views showing pixel structures according to another exemplary embodiment of the inventive concept.

A pixel structure in FIG. 8A is a modified example of the pixel structure in FIG. 2A, and a pixel structure in FIG. 8B is a modified example of the pixel structure in FIG. 2B. The sub-pixels included in the first and second pixels P1 and P2 in FIGS. 2A and 2B are formed in a stripe structure; however, the sub-pixels in the first and second pixels P1 and P2 in FIGS. 8A and 8B may not be formed in a stripe structure. For example, the blue sub-pixels B1 and B2 may be formed long in a vertical direction, and the red sub-pixel R and the green sub-pixel G may be formed long in a horizontal direction beside the blue sub-pixels B1 and B2. The red sub-pixel R and the green sub-pixel G may be located adjacent to each other vertically.

As described above, according to the one or more of the above exemplary embodiments, a display apparatus and a method and an apparatus for controlling the display apparatus is very useful to a user because the display apparatus and the method and the apparatus for controlling the display apparatus may wake a user up or help the user fall asleep depending on a setting of the display mode.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various suitable changes in form and details may be made therein without departing from the spirit and scope as defined by the following claims, and equivalents thereof.

What is claimed is:

1. A display control method of a display panel, the display control method comprising:
setting a display mode of the display panel to one selected from a first mode using a first blue sub-pixel, a second mode using a second blue sub-pixel, and a third mode using the first blue sub-pixel and the second blue sub-pixel to emit blue light; and
generating an output signal to use the first blue sub-pixel when the display mode is the first mode, to use the second blue sub-pixel for the second mode, and to use both the first blue sub-pixel and the second blue sub-pixel for the third mode,
wherein the display panel is configured to emit light corresponding to the output signal,
wherein the display panel comprises a first pixel comprising the first blue sub-pixel and a second pixel comprising the second blue sub-pixel, the second blue sub-pixel being configured to emit light having a wavelength different from that of the first blue sub-pixel,
wherein the first pixel and the second pixel are alternately located,
wherein the second pixel is adjacent to the first pixel,
wherein the first pixel comprises a first sub-pixel group comprising a red sub-pixel and a green sub-pixel, and a second sub-pixel group comprising the first blue sub-pixel and a green sub-pixel,
wherein the second pixel comprises a third sub-pixel group comprising a red sub-pixel and a green sub-pixel, and a fourth sub-pixel group comprising the second blue sub-pixel and a green sub-pixel, wherein the display panel is driven according to the first mode or the second mode, for controlling a sleep or a wake up of a viewer, and the display panel is driven according to the third mode for a general display mode, wherein, in the first mode, a value equal to a pixel value assigned to the second blue sub-pixel of the second pixel in an original image is added to pixel values of the first blue sub-pixels of adjacent first pixels around the second pixel to increase pixel values of the first blue sub-pixels of adjacent first pixels around the second pixel, and the pixel value assigned to the second blue sub-pixel of the second pixel in the original image is changed to 0, and wherein, in the second mode, a value equal to a pixel value assigned to the first blue sub-pixel of the first pixel in an original image is added to pixel values of the second blue sub-pixels of adjacent second pixels around the first pixel to increase pixel values of the second blue sub-pixels of adjacent second pixels around the first pixel, and the pixel value assigned to the first blue sub-pixel of the first pixel in the original image is changed to 0.

2. The display control method of claim 1, wherein a center wavelength of light emitted from the first blue sub-pixel is lower than a center wavelength of light emitted from the second blue sub-pixel.

3. The display control method of claim 1, wherein in the setting the display mode of the display panel, a current state is determined as day or night, wherein when the current state is day, the display mode is set to the second mode or the third mode and when the current state is night, the display mode is set to the first mode.

4. The display control method of claim 3, wherein in the setting the display mode of the display panel, a current state is determined as day or night based on at least one selected from a current time, a pre-set display mode change cycle, or external illumination, and the display mode is set based on the current state.

5. A display control apparatus of a display panel, the apparatus comprising:

a display mode controller configured to set a display mode of the display panel to one selected from a first mode using a first blue sub-pixel, a second mode using a second blue sub-pixel, and a third mode using both the first blue sub-pixel and the second blue sub-pixel to emit blue light; and an output signal generator configured to generate an output signal to use the first blue sub-pixel when the display mode is the first mode, to use the second blue sub-pixel for the second mode, and to use the first blue sub-pixel and the second blue sub-pixel for the third mode, wherein the display panel is configured to emit light corresponding to the output signal, wherein the display panel comprises a first pixel comprising the first blue sub-pixel and a second pixel comprising the second blue sub-pixel, the second blue sub-pixel being configured to emit light having a wavelength different from that of the first blue sub-pixel, wherein the first pixel and the second pixel are alternately located, wherein the second pixel is adjacent to a first pixel, wherein the first pixel comprises a first sub-pixel group comprising a red sub-pixel and a green sub-pixel, and a second sub-pixel group comprising the first blue sub-pixel and a green sub-pixel, wherein the second pixel comprises a third sub-pixel group comprising a red sub-pixel and a green sub-pixel, and a fourth sub-pixel group comprising the second blue sub-pixel and a green sub-pixel, wherein the display mode controller configured to set the first mode or the second mode for controlling a sleep or a wake up of a viewer, and the display mode controller configured to set the third mode for a general display mode, wherein, in the first mode, a value equal to a pixel value assigned to the second blue sub-pixel of the second pixel in an original image is added to pixel values of the first blue sub-pixels of adjacent first pixels around the second pixel to increase pixel values of the first blue sub-pixels of adjacent first pixels around the second pixel, and the pixel value assigned to the second blue sub-pixel of the second pixel in the original image is changed to 0, and wherein, in the second mode, a value equal to a pixel value assigned to the first blue sub-pixel of the first pixel in an original image is added to pixel values of the second blue sub-pixels of adjacent second pixels around the first pixel to increase pixel values of the second blue sub-pixels of adjacent second pixels around the first pixel, and the pixel value assigned to the first blue sub-pixel of the first pixel in the original image is changed to 0.

6. The display control apparatus of claim 5, wherein a center wavelength of light emitted from the first blue sub-pixel is lower than a center wavelength of light emitted from the second blue sub-pixel.

7. The display control apparatus of claim 6, wherein the display mode controller is further configured to determine a current state as day or night based on at least one selected from a current time, a pre-set display mode change cycle, or external illumination, and to set the display mode based on the current state.

8. The display control apparatus of claim 5, wherein the display mode controller is further configured to determine a current state as day or night, and when the current state is day, to set the display mode to the second mode or the third mode, and when the current state is night, to set the display mode to the first mode.

9. The display control apparatus of claim 8, wherein the display mode controller is further configured to determine a current state as day or night based on at least one selected from a current time, a pre-set display mode change cycle, or external illumination, and to set the display mode based on the current state.

10. The display control apparatus of claim 5, wherein the display mode controller is further configured to determine a current state as day or night based on at least one selected from a current time, a pre-set display mode change cycle, or external illumination, and to set the display mode based on the current state.

* * * * *